United States Patent
Bergersen

(12) 
(10) Patent No.: US 6,582,225 B1
(45) Date of Patent: Jun. 24, 2003

(54) DENTAL DIAGNOSIS AND DISPENSING APPARATUS AND A SYSTEM AND A METHOD FOR PROVIDING SAME

(76) Inventor: Earl O. Bergersen, 950 Green Bay Rd., Winnetka, IL (US) 60093

(*) Notice: Subject to any disclaimer, the term of this patent is extended or adjusted under 35 U.S.C. 154(b) by 0 days.

(21) Appl. No.: 09/686,142

(22) Filed: Oct. 11, 2000

(51) Int. Cl.[7] ................................................ A61C 3/00
(52) U.S. Cl. ................................. 433/2; 433/6; 433/24
(58) Field of Search ............................. 433/3, 2, 6, 24, 433/213, 215, 214

(56) References Cited

U.S. PATENT DOCUMENTS

| | | | |
|---|---|---|---|
| 3,898,736 A | | 8/1975 | Bergersen |
| 3,939,598 A | | 2/1976 | Bergersen |
| 4,073,061 A | | 2/1978 | Bergersen |
| 5,037,295 A | | 8/1991 | Bergersen |
| 5,341,291 A | * | 8/1994 | Roizen et al. ............... 128/920 |
| 5,453,009 A | * | 9/1995 | Feldman ..................... 433/215 |
| 5,458,487 A | * | 10/1995 | Komatsu et al. ............... 433/71 |
| 5,882,192 A | | 3/1999 | Bergersen |
| 6,089,868 A | * | 7/2000 | Jordan et al. ............... 433/215 |
| 6,099,314 A | * | 8/2000 | Kopelman et al. ........... 433/213 |
| 6,217,325 B1 | * | 4/2001 | Chisti et al. ................. 433/215 |
| 6,217,334 B1 | * | 4/2001 | Hultrgen ..................... 433/215 |
| 6,227,850 B1 | * | 5/2001 | Chisti et al. ................. 433/213 |

* cited by examiner

*Primary Examiner*—Cary E. O'Connor
(74) *Attorney, Agent, or Firm*—Patents +TMS, P.C.

(57) ABSTRACT

An apparatus, a system and a method are provided for providing a dental diagnosis and/or a dental appliance to a user by examining a portion of a mouth of the user. To this end, the apparatus, system and method evaluate images whether digital, still, video, digital x-ray or the like, of the portion of the mouth to determine if a medical condition may be cured and/or corrected by a dental appliance stored within a machine and capable of being dispensed from the machine. The apparatus, system and method may evaluate the condition of a user from images of a single tooth. Moreover, evaluation of the images may be performed by the central processing unit of the apparatus or by an outside source, by having the images transmitted via, for example, the internet, electronic mail, telephony, satellite, or other means, to another computer or individual. The user may also take images of his mouth while positioning a ruler or other measuring device adjacent to the mouth. The images may then be transmitted to an individual and/or a central processing unit for diagnosis. In addition, the system may provide a wafer or tray which the user may position in his mouth to make an impression. The wafer or tray, or an image of the wafer or tray, may then be sent to an individual and/or a central processing unit. Also, a user may position a film within his mouth and transmit the film or an image of the film to an individual and/or central processing unit.

59 Claims, 5 Drawing Sheets

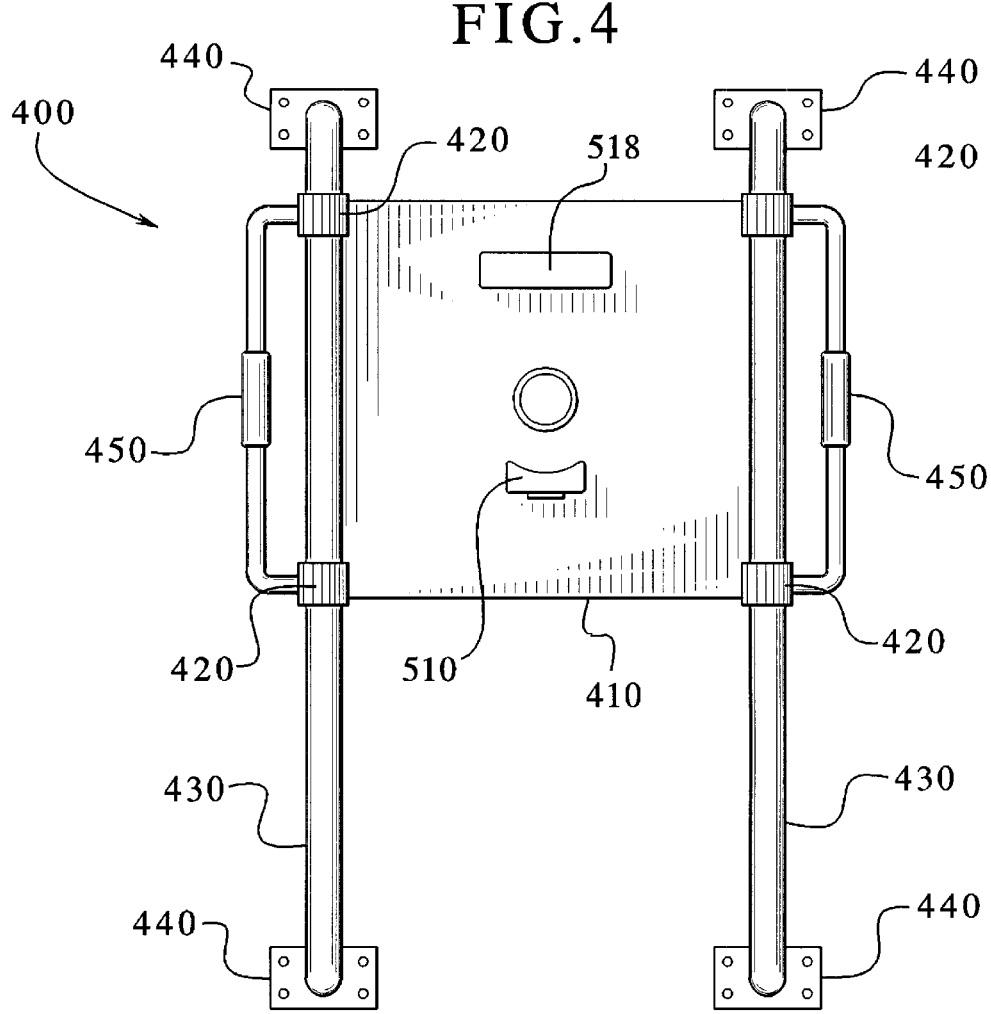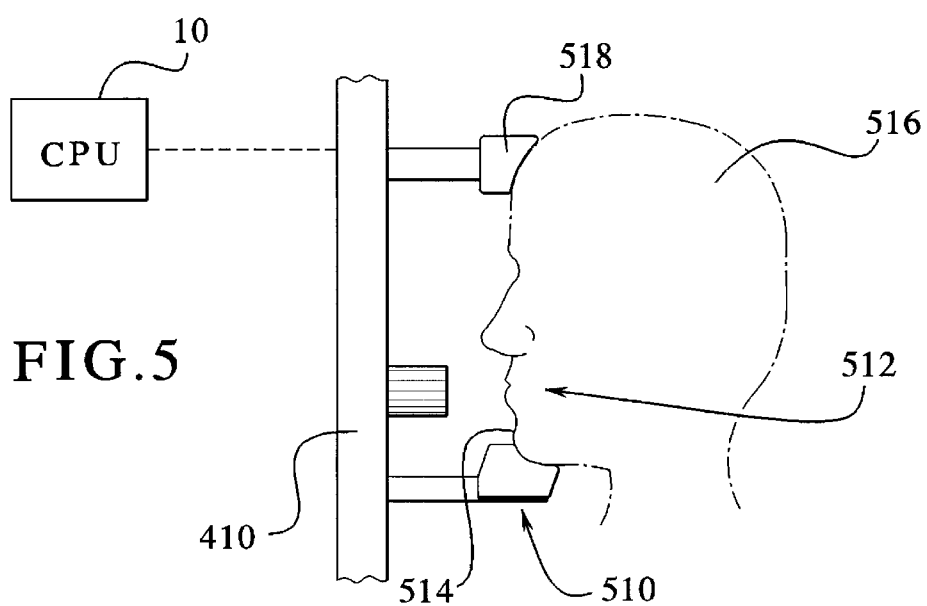

DENTAL DIAGNOSIS AND DISPENSING APPARATUS AND A SYSTEM AND A METHOD FOR PROVIDING SAME

BACKGROUND OF THE INVENTION

The present invention generally relates to an apparatus, a system and a method that provides a dental diagnosis and/or a dental appliance to a user. More specifically, the present invention provides an apparatus, a system and a method that allows one or more users to have a portion of their mouths examined and subsequently receive a diagnosis of their medical conditions. The present invention further provides an apparatus, a system and a method for one or more users to receive a corrective dental apparatus depending on their medical conditions. In addition, the present invention provides a means to receive payment for the services.

It is, of course, generally known to analyze teeth of an individual. Throughout the life of an individual, teeth often require corrective measures to remain healthy or to correct defects with which an individual may be born or develop at later ages, such as an overbite, overjet, crowding, and/or spacing of teeth. The need for corrective measures for teeth has brought about various procedures, examinations, diagnoses and the like, such as those provided by a dentist or orthodontist, as well as corrective measures in the form of dental appliances which may be worn in the mouth.

However, dentists and orthodontists often are inaccessible due to a person's schedule, geographic location or various other reasons. Moreover, such professionals may be unaffordable to some individuals. In other cases, such as in third world countries, dentists and orthodontists are inaccessible to some individuals for reasons such as poverty or the inability to travel to a dental office. Consequently, those living in third world countries are often devoid of quality dental care and/or necessary corrective measures, including diagnosis and advice.

It is also generally known to provide a machine that examines a mouth and/or teeth of a user who seeks a diagnosis and/or corrective measures. Such a machine instructs users as to whether they require a dental appliance. The machine functions in an environment completely independent of a dental office or the like. However, known machines are complex and are limited in their scope of examination. For example, known machines may take images of the entire interior of the mouth. As a result, the examination process is tedious and time-consuming. Moreover, the accuracy of the diagnosis of known machines is dependent on the angle at which images of the interior of the mouth are taken. In addition, the data taken by known machines is compared to data stored in the machine. With such machines, the processing unit within the machine and its associated programming is the only source for providing a user with a diagnosis.

A need, therefore, exists for an improved apparatus, system and method for providing an improved dental diagnosis. In addition, a need exists for an apparatus, a system and a method for providing improved image data evaluation by submission of image data, taken, for example, by a digital camera, digital x-ray or the like, via the internet, electronic mail, telephony means, satellite or the like, for further evaluation and/or diagnosis as well as remote dispensing of a corrective appliance, if necessary.

SUMMARY OF THE INVENTION

The present invention provides an apparatus, a system and a method as well as a simplified impression or photographic technique that allows one or more users to have portions of their mouths examined and/or receive a diagnosis of their condition. The present invention further provides an apparatus, a system and a method or impression or photographic technique enabling a user to receive a corrective dental appliance depending on their condition. To this end, in an embodiment of the present invention, an apparatus provides a diagnosis of an orthodontic state of a user and dispenses one of a plurality of dental appliances worn on a mouth of the user or a single one-size fits all appliance. The apparatus has an image capturing device wherein the image capturing device obtains an image of a portion of the mouth of the user and produces a signal indicative of the image. The apparatus further has a central processing unit programmed with data regarding orthodontic conditions. The central processing unit classifies the signal sent by the image capturing device into a plurality of orthodontic states.

In an embodiment, the apparatus further has input means for entering information into the central processing unit.

In an embodiment, the apparatus further has a payment device programmed to receive payment from the user.

In an embodiment, the image of the portion of the mouth of the user is an image of a single tooth of the user.

In an embodiment, the central processing unit is located remote from the image capturing device.

In an embodiment, the portion of the mouth of the user is from a midline of a set of teeth of the user to a back portion of an interior of the mouth of the user.

In another embodiment of the present invention, an apparatus provides a diagnosis of an orthodontic state of a user. The apparatus has an image capturing device wherein the image capturing device obtains an image of a portion of a mouth of the user and produces a signal indicative of the image. The apparatus further has a central processing unit programmed with data regarding orthodontic conditions wherein the central processing unit provides a diagnosis to the user of the orthodontic state of the user based on the image obtained by the image capturing device wherein the portion of the mouth of the user is a single tooth of the user.

In an embodiment, the apparatus further has input means entering information into the central processing unit.

In an embodiment, the apparatus further has a payment device programmed to receive payment from the user.

In an embodiment, the central processing unit is programmed with data regarding orthodontic conditions wherein the central processing unit classifies the signal sent by the image capturing device into a plurality of orthodontic states.

In an embodiment, the central processing unit is located remote from the image capturing device.

In another embodiment of the present invention, an apparatus provides a diagnosis of an orthodontic state of a user. The apparatus has an image capturing device wherein the image capturing device obtains an image of a portion of the mouth of the user wherein the portion of the mouth of the user is from a midline of a set of teeth of the user to a back portion of an interior of the mouth of the user, the image capturing device producing a signal indicative of the image. The apparatus further has a central processing unit programmed with data regarding orthodontic conditions wherein the central processing unit classifies the signal sent by the image capturing device into a plurality of orthodontic states.

In an embodiment, the apparatus further has input means for entering information into the central processing unit.

In an embodiment, the apparatus further has a payment device programmed to receive payment from the user.

In an embodiment, the central processing unit is located remote from the image capturing device.

In another embodiment of the present invention, a system provides a diagnosis of an orthodontic state of a user. The system has an apparatus having an image capturing device wherein the image capturing device obtains an image of a portion of a mouth of the user. The apparatus further has a data transmission device capable of transmitting the image as a signal indicative of the image. The system further has a central processing unit located remote from the apparatus programmed with statistical data regarding orthodontic conditions wherein the central processing unit communicates with the apparatus and receives the signal from the apparatus.

In an embodiment, the system further has input means for entering information into the data transmission device.

In an embodiment, the system further has a payment device programmed to receive payment from the user.

In an embodiment, the central processing unit is programmed with data regarding orthodontic conditions. The central processing unit classifies the signal sent by the image capturing device into a plurality of orthodontic states.

In an embodiment, the central processing unit is programmed to diagnose the orthodontic state of the user based on the age of the user.

In an embodiment, the portion of the mouth of the user is a single tooth of the user.

In another embodiment of the present invention, a method provides a diagnosis of an orthodontic state of a user. The method comprises the steps of: providing a plurality of dental appliances wherein one or more of the dental appliances is worn in the mouth of the user; providing an image capturing device wherein the image capturing device obtains an image of the portion of the mouth of the user and produces a signal indicative of the image; providing a central processing unit programmed with data regarding orthodontic conditions wherein the central processing unit classifies the signal sent by the image capturing device into a plurality of orthodontic states corresponding to each of a type and size of the dental appliances; obtaining the image of the portion of the mouth of the user; and transmitting the image to the central processing unit.

In an embodiment, the image of the portion of the mouth is of a single tooth of the user.

In an embodiment, the central processing unit is located remote from the image capturing device.

In another embodiment of the present invention, a method provides a diagnosis of an orthodontic state of a user. The method comprises the steps of: providing a plurality of dental appliances wherein each of the dental appliances is worn in the mouth of a user; providing an image capturing device wherein the image capturing device obtains an image of the portion of the mouth of the user and produces a signal indicative of the image; providing a central processing unit programmed with data regarding orthodontic conditions wherein the central processing unit classifies the signal sent by the image capturing device into a plurality of orthodontic states; obtaining the image of the portion of the mouth of the user; and transmitting the image to the central processing unit.

In an embodiment, the image of the portion of the mouth is of a single tooth of the user.

In an embodiment, the central processing unit is located remote from the image capturing device.

In an embodiment, the portion of the mouth is from a single tooth of the user to a midline of the user.

In another embodiment of the present invention, a method provides a diagnosis of an orthodontic state of a user. The method comprises the steps of: providing an image capturing device wherein the image capturing device obtains an image of a portion of the mouth of the user and produces a signal indicative of the image; providing a central processing unit programmed with data regarding orthodontic conditions wherein the central processing unit provides a diagnosis to the user of the orthodontic state of the user based on the signal transmitted by the image capturing device; obtaining the image of the portion of the mouth of the user wherein the portion of the mouth is a single tooth of the user; and transmitting the image to the central processing unit.

In an embodiment, the central processing unit is programmed with data regarding orthodontic conditions wherein the central processing unit classifies the signal sent by the image capturing device into a plurality of orthodontic states.

In an embodiment, the central processing unit is located remote from the image capturing device.

In another embodiment of the present invention, a method provides a diagnosis of an orthodontic state of a user. The method comprises the steps of: providing an apparatus having an image capturing device wherein the image capturing device obtains an image of a portion of a mouth of the user, the apparatus further having a data transmission device capable of transmitting a signal indicative of the image or a set of data of the user to a central processing unit; providing a central processing unit located remote from the apparatus programmed with statistical data regarding orthodontic conditions; obtaining the image of the portion of the mouth of the user; and transmitting the image to the central processing unit.

In an embodiment, the portion of the mouth of the user is a single tooth of the user.

In an embodiment, the portion of the mouth of the user is from a midline of a set of teeth of the user to a back portion of an interior of the mouth of the user.

In an embodiment, the central processing unit is programmed to diagnose the orthodontic state of the user based on the age of the user.

In an embodiment, the central processing unit is programmed with data regarding orthodontic conditions wherein the central processing unit classifies the signal sent by the image capturing device into a plurality of orthodontic states.

In another embodiment of the present invention, a method provides a diagnosis of an orthodontic state of a user, the method has the steps of: providing an image capturing device wherein the image capturing device obtains an image of a portion of the mouth of the user wherein the portion of the mouth of the user is from a midline of a set of teeth of the user to a back portion of an interior of the mouth of the user, the image capturing device producing a signal indicative of the image; providing a central processing unit programmed with data regarding orthodontic conditions wherein the central processing unit provides a diagnosis to the user of the orthodontic state of the user based on the signal transmitted by the image capturing device; obtaining the image of the portion of the mouth of the user wherein the portion of the mouth is a single tooth of the user; and transmitting the image to the central processing unit.

In an embodiment, the central processing unit is programmed with data regarding orthodontic conditions wherein the central processing unit classifies the signal sent by the image capturing device into a plurality of orthodontic states.

In an embodiment, the central processing unit is located remote from the image capturing device.

In another embodiment of the present invention, an apparatus provides a diagnosis of an orthodontic state of a user. The apparatus has a data input device that receives input as to an age of the user. The apparatus further has a central processing unit programmed with data regarding orthodontic conditions wherein the central processing unit diagnoses the orthodontic state of the user based on the age of the user.

In an embodiment, the central processing unit is located remote from the image capturing device.

In another embodiment of the present invention, a method provides a diagnosis of an orthodontic state of a user. The method has the steps of: providing an input device; inputting an age of the user in the input device; providing a central processing unit programmed with data regarding orthodontic conditions and receiving information from the input device; and providing a diagnosis to the user of the orthodontic state of the user based on the age of the user.

In an embodiment, the central processing unit is located remote from the image capturing device.

In another embodiment of the present invention, an apparatus provides a diagnosis of an orthodontic state of a user. The apparatus has an image capturing device attached to a rod or rods and movable on the rod or rods wherein the image capturing device obtains an image of the portion of the mouth of the user and produces a signal indicative of the image. The apparatus further has a central processing unit programmed with data regarding orthodontic conditions wherein the central processing unit receives the signal sent by the image capturing device and classifies the signal into a plurality of orthodontic states.

In an embodiment, the central processing unit is located remote from the image capturing device.

In an embodiment, the image is of a single tooth of the user.

In an embodiment, the image is from a midline of teeth of the user to a back portion of the mouth of the user.

In another embodiment of the present invention, a method provides a diagnosis of an orthodontic state of a user. The method has the steps of: providing a wafer; providing a central processing unit programmed with data regarding orthodontic conditions; positioning the wafer within a mouth of the user and making an impression of a tooth of the user; capturing an image of the wafer; and transmitting the image of the wafer to the central processing unit.

In another embodiment of the present invention, a method provides a diagnosis of an orthodontic state of a user. The method has the steps of: providing a film; providing a central processing unit programmed with data regarding orthodontic conditions; positioning the film within a mouth of the user and making an impression of a tooth of the user; capturing an image of the photosensitive film; and transmitting the image of the film to the central processing unit.

In another embodiment of the present invention, a method provides a diagnosis of an orthodontic state of a user. The method has the steps of: providing a central processing unit programmed with data regarding orthodontic conditions; providing an image capturing device wherein the image capturing device obtains an image of a portion of the mouth of the user; transmitting the image of a portion of the mouth of the user to the central processing unit; and altering the image.

In another embodiment of the present invention, a method provides a diagnosis of an orthodontic state of a user. The method has the steps of: providing an output device; providing a central processing unit programmed with data regarding orthodontic conditions; and querying the user regarding the orthodontic state of the user via the output device.

In an embodiment, the method has the further steps of: providing an input device; and inputting a response from the user to a query from the central processing unit.

In an embodiment, the method has the further step of transmitting the response to the central processing unit.

In another embodiment of the present invention, a method provides a diagnosis of an orthodontic state of a user. The method has the steps of: providing a tray; providing a central processing unit programmed with data regarding orthodontic conditions; positioning the tray within a mouth of the user and making an impression of a tooth of the user; capturing an image of the tray; and transmitting the image of the tray to the central processing unit.

In another embodiment of the present invention, an apparatus provides a diagnosis of an orthodontic state of a user. The apparatus has an image capturing device wherein the image capturing device obtains an image of a portion of the mouth of the user and produces a signal indicative of the image. The apparatus further has a focusing mechanism by which the image capturing device is able to focus. The apparatus further has a central processing unit programmed with data regarding orthodontic conditions and further programmed to diagnose the orthodontic state of the user based on a distance between the focusing mechanism and the user.

In another embodiment of the present invention, a method provides a diagnosis of an orthodontic state of a user. The method comprises the steps of: providing an image capturing device wherein the image capturing device obtains an image of a portion of the mouth of the user and produces a signal indicative of the image; providing a focusing mechanism by which the image capturing device is able to focus; providing a central processing unit programmed with data regarding orthodontic conditions and further programmed to diagnose the orthodontic state of the user based on a distance between the focusing mechanism and the user; positioning the focusing mechanism toward the mouth of the user; obtaining the image of the portion of the mouth of the user; and transmitting the image to the central processing unit.

In another embodiment of the present invention, a method provides a diagnosis of an orthodontic state of a user. The method comprises the steps of: providing a wafer; providing an image capturing device wherein the image capturing device obtains an image and produces a signal indicative of the image; providing a central processing unit located remote from the image capturing device programmed with data regarding orthodontic conditions; positioning the wafer within a mouth of the user and making an impression of a tooth of the user; capturing an image of the wafer; and transmitting the image of the wafer to the central processing unit.

In another embodiment of the present invention, a method provides a diagnosis of an orthodontic state of a user. The method comprises the steps of: providing a tray; providing an image capturing device wherein the image capturing device obtains an image and produces a signal indicative of the image; providing a central processing unit located remote from the image capturing device programmed with data regarding orthodontic conditions; positioning the tray within a mouth of the user and making an impression of a tooth of the user; capturing an image of the tray; and transmitting the image of the tray to the central processing unit.

In another embodiment of the present invention, a method provides a diagnosis of an orthodontic state of a user. The method comprises the steps of: providing an impression device capable of obtaining an impression of a tooth of the user; providing an image capturing device wherein the image capturing device obtains an image and produces a signal indicative of the image; providing a central processing unit programmed with data regarding orthodontic conditions; positioning the impression device within a mouth of the user and making an impression of a tooth of the user; capturing an image of the impression device; and transmitting the image of the impression device to the central processing unit.

In another embodiment of the present invention, a method provides a diagnosis of an orthodontic state of a user. The method comprises the steps of: providing an impression device capable of obtaining an impression of a tooth of the user; providing an image capturing device wherein the image capturing device obtains an image and produces a signal indicative of the image; providing a central processing unit located remote from the image capturing device programmed with data regarding orthodontic conditions; positioning the impression device within a mouth of the user and making an impression of a tooth of the user; capturing an image of the impression device; and transmitting the image of the impression device to the central processing unit.

It is, therefore, an advantage of the present invention to provide an apparatus, a system and a method for providing a user with a diagnosis of his dental condition.

Another advantage of the present invention is to provide an apparatus, a system and a method for dispensing a corrective dental appliance for a user.

Yet another advantage of the present invention is to provide an apparatus, a system and a method that allows evaluation of the mouth of the user based on results extrapolated from an image of a single tooth.

Further, an advantage of the present invention is to provide an apparatus, a system and a method for evaluating images of the portion of the mouth of the user by transmitting the images to a remote central processing unit and/or a remote individual.

Another advantage of the present invention is to provide an apparatus, a system and a method for providing evaluation and/or diagnosis of teeth for users throughout the world, including individuals of various races.

A still further advantage of the present invention is to provide an apparatus, a system and a method for dispensing corrective dental appliances based on categories of severity regarding dental conditions to improve efficiency of the evaluation.

Yet another advantage of the present invention is to provide an apparatus, a system and a method for communicating with the user and diagnosing temporomandibular joint conditions, by verbal means, such as a speaker system or the like, or written means.

Additional features and advantages of the present invention are described in, and will be apparent from, the detailed description of the presently preferred embodiments and from the drawings.

BRIEF DESCRIPTION OF THE DRAWINGS

FIG. 4 illustrates a perspective view of an apparatus in an embodiment of the present invention.

FIG. 5 illustrates a side view of an apparatus in an embodiment of the present invention.

DETAILED DESCRIPTION OF THE PRESENTLY PREFERRED EMBODIMENTS

The present invention generally relates to an apparatus, a system and a method that provides a dental evaluation and/or diagnosis and/or a dental appliance to a user by examining a portion of a mouth of the user. To this end, the apparatus, system and method evaluate images or impressions of the portion of the mouth to determine if a medical condition may be cured and/or corrected by a dental appliance stored within a machine and capable of being dispensed from the machine, or sent directly to the user from a remote location or dispensed by a dealer.

Figure 1:
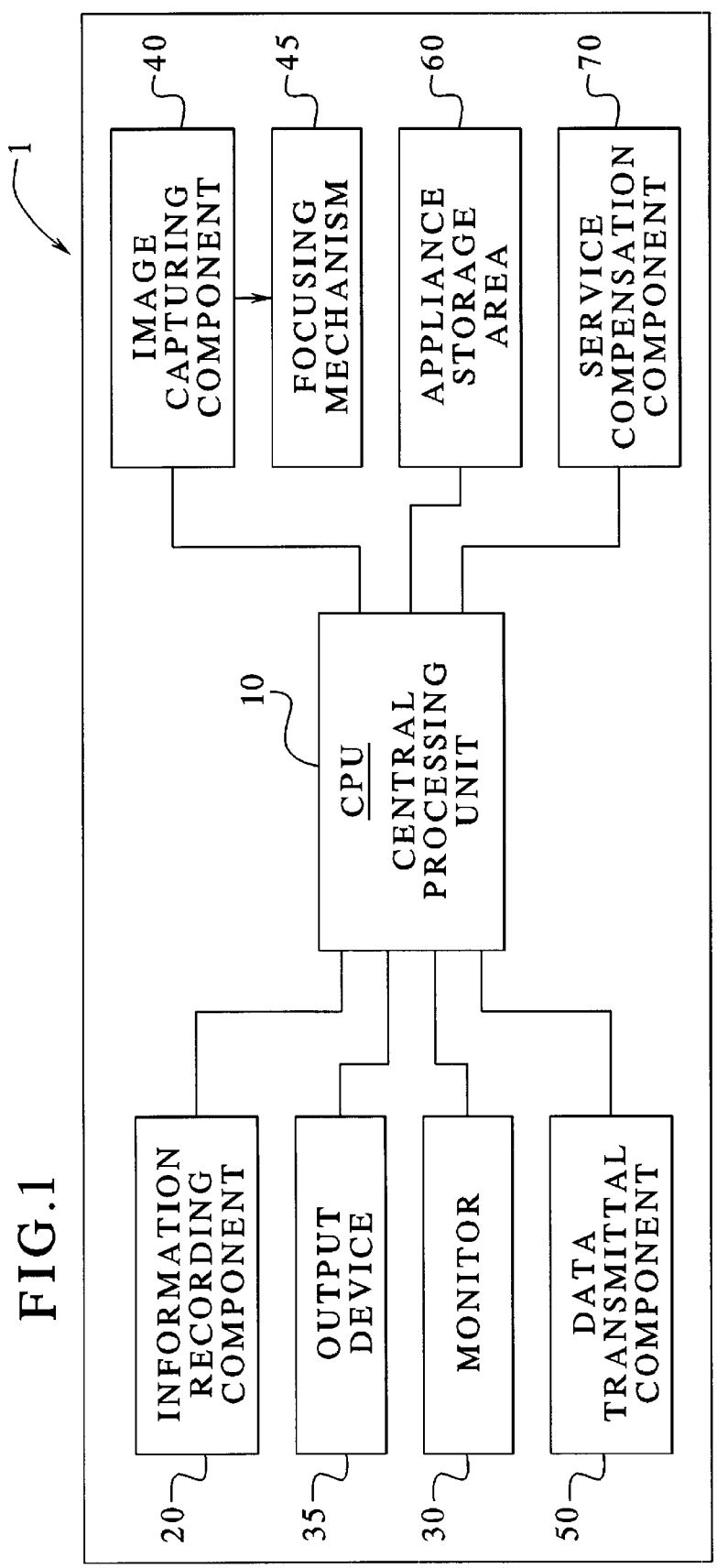
FIG. 1 illustrates a black box diagram of a system in an embodiment of the present invention.

Referring now to the drawings wherein like numerals refer to like parts, FIG. 1 illustrates a system 1 having components including a central processing unit 10 (hereinafter referred to as a "CPU"). The CPU 10 may evaluate data transmitted to the CPU 10 by the components of the system 1. Further, the CPU 10 may control the components of the system 1. The CPU 10 may be programmed by one skilled in the art to evaluate data as well as control the components of the system 1.

In addition, the system 1 may include an information recording component 20 (hereinafter referred to as "IRC"). The IRC 20 may include an input device as part of the IRC 20 for a user to enter information to be processed by the CPU 10 prior to, during, or after examination by the system 1. Such information may include, but is not limited to, the user's age, race, sex, etc. The input device of the IRC 20 may include a keyboard or any other means for entering characters or information to be processed by the CPU 10.

The system 1 may also have a monitor 30 which may allow the user to see the information entered by the user into the IRC 20. In addition, the monitor 30 may display instructions for the user relating to proper use of the system 1.

The system may also have an output device 35 such as, for example, a speaker, or other component known by those skilled in the art. The output device 35 may communicate verbally with the user and may query the user as to the orthodontic conditions of the user.

The system 1 may also provide an image capturing component 40 (hereinafter referred to as "ICC"). The ICC 40 may take images of a portion of an interior of a mouth and/or exterior of a face of the user. The ICC 40 may take images, whether, digital, still, video, digital x-ray or the like, by means of a camera or any other image capturing device known by those skilled in the art. The images from the ICC 40 may be transferred to the CPU 10 for evaluation.

The system may also have a focusing mechanism 45 used in conjunction with the ICC 40. The focusing mechanism 45 may consist of a lens or the like. The CPU 10 may estimate the distance from the digital x-ray, photographic image, or other type of image to the surface of a tooth by means of the focusing mechanism 45 and may then estimate the degree of enlargement or reduction required for a diagnosis in terms of calculating the proper size of a tooth or teeth of the user.

The images from the ICC 40, or information otherwise gathered by the system 1 may be transmitted, electronically or otherwise, by a data transmittal component 50 (hereinafter referred to as "DTC"). The DTC 50 may transmit images or data to another location, for example, via the internet, electronic mail or other means, for evaluation by another system or individual, such as a doctor, dentist, orthodontist or the like. The DTC 50 may be implemented by one skilled in the art such that the DTC 50 may transmit images and/or data by, for example, the internet, telephony, satellite or other means.

The system 1 may also have a dental appliance storage area 60. The area 60 may house a variety of dental appliances which may be dispensed to the user by the system 1. The CPU 10 of the system 1 may store information regarding the severity of a medical condition. The severity may be identified in one of three categories: minimal, moderate or severe. For example, the CPU 10 may store information, such as medical standards regarding the degree of an overbite. The CPU 10 may determine if the overbite is minimal, moderate, or severe based upon images from the ICC 40. To this end, ranges may be established for each of the three categories. Information regarding the user and images from the ICC 40 may be analyzed by appropriate software installed in the CPU 10 to determine in which category the user is classified. An overbite that is more than minimal may be treatable by a corrective dental appliance. If the CPU 10 determines that the overbite of the user is greater than minimal, a corrective dental appliance from the dental appliance storage area 60 may be dispensed to the user. However, if the CPU 10 determines that the degree of overbite is a maximum amount and/or further determines that the age of the user is greater than 15 years, the CPU 10 may choose to deny the user a diagnosis and/or dental appliance.

In addition, the system 1 may also have a service compensation component 70 (hereinafter referred to as "SCC"). The SCC 70 may allow the user to make payment for the services rendered by the system 1. The SCC 70 may include, for example, a credit card processing means that may allow the user to pay for the services rendered by, for example, a credit card, a debit card or the like. In addition, the SCC 70 may process cash, negotiable instruments or the like as payment for use of the system 1 and/or receipt of the appliance.

Figure 2:
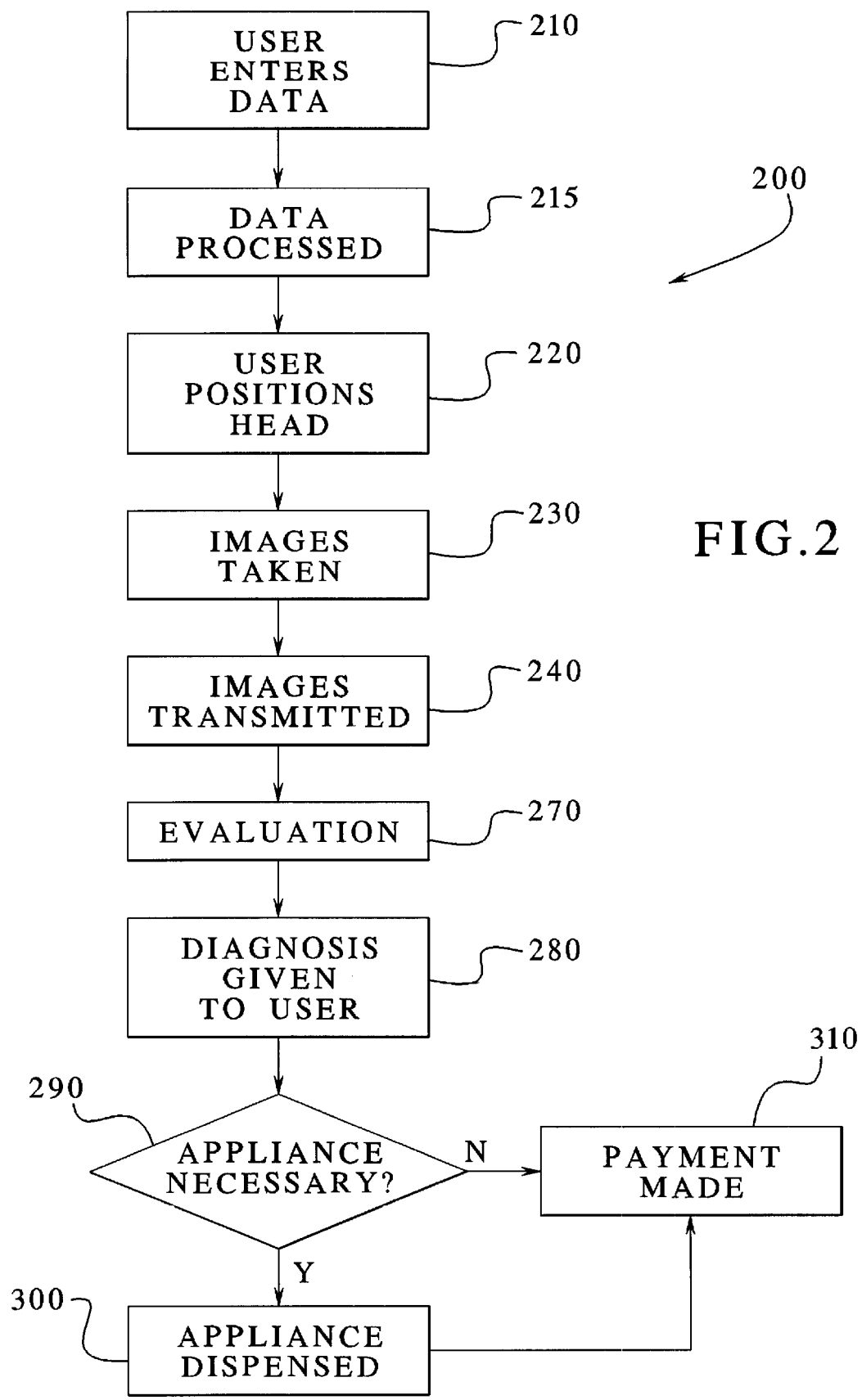
FIG. 2 illustrates a black box diagram of a method in an embodiment of the system of the present invention.

Referring now to FIG. 2, a flowchart 200 of the system 1 is illustrated. The system 1 may provide the user with a dental examination and/or diagnosis regarding a condition. Use of the system 1 may be initiated by, for example, entry of personal information regarding the user, as shown at step 210, into the IRC 20. The personal information may be processed, as shown at step 215, by the CPU 10 to correlate with predetermined dental standards for individuals of varying age, race, sex, etc., which may already be stored in the CPU 10.

The user may then position his head, as shown at step 220, onto, for example, a head rest, chin rest, or the like, associated with the system for examination. Next, images of the interior of the mouth of the user may be taken, as shown at step 230. The images may be taken by, for example, a digital camera, digitized x-rays or the like.

The images may then be transmitted, as shown at step 240, to either an outside source such as a doctor, dentist, orthodontist and/or other trained professional, the CPU 10, or both, for evaluation, as shown in step 270. The transmission may be made by, for example, the internet, electronic mail, telephony, satellite, or other means. Alternatively, a local transmission to the CPU 10 of the system 1 may conduct the analysis and/or diagnosis.

The system and method of the present invention may use different images to determine medical conditions that the user may be experiencing. For example, the CPU 10 may evaluate a frontal view image to determine the midlines, the specific front incisor to calculate its accurate mesio-distal width and, therefore, to accurately calculate the sizes of all other deciduous and permanent teeth, erupted and unerupted according to medical standards stored within the CPU 10. In addition, the frontal view may be used to determine whether the user suffers from overbite, gingival recession or normality of the lower incisors. Furthermore, the frontal view may be used to determine the rotation or crowding or spacing of incisors, x-bites of the anterior or posterior teeth.

The CPU 10 may analyze an image having an occlusal view of the portion of the mouth of the user for rotations of anterior teeth as well as to determine the widths of teeth and the severity of crowding and spacing of anterior teeth. The CPU 10 may identify the midline of the user and be able to count the teeth of the user from the midline in accordance with specific anatomic characteristics of each tooth of the user to determine which teeth are present and which teeth are absent from the mouth of the user.

The CPU 10 may analyze an image having a lateral view of the portion of the mouth of the user to measure spaces where posterior teeth are generally present but may not yet be fully erupted. Also, the CPU 10 may analyze an image of the lateral view to determine cross-bites present in the posterior segment and overjet severity. In addition, the CPU 10 may analyze an image of the lateral view to determine whether the user has properly closed his mouth. If the user has improperly closed his mouth, the CPU 10 and/or the system 1 may direct the user how to properly compensate for the inaccurate position to obtain a more accurate measure of overjet and overbite. The CPU 10 may also analyze an image of the lateral view of the face of the user to measure face height and the effect of the overjet on the profile of the face. The frontal facial view may be used to determine lip compatibility on closure and/or face height and lower jaw deviation when opening the jaw. The lateral facial view is used for jaw relationship in an antero-posterior direction.

The system 1 of the present invention may also evaluate and predict the sizes of all of the teeth in the mouth and diagnose the adequacy of space for incoming teeth of the user from merely capturing an image of a single tooth. In fact, the system 1 of the present invention may determine the size of other teeth based on the size of a single tooth as well as predetermined dental standards such as those illustrated in Appendix A and stored within the CPU 10 to allow the CPU 10 to extrapolate the various sizes of the remainder of teeth in the mouth of the user. Moreover, the CPU 10 may discern whether the front tooth is reliable for extrapolating the sizes of the other teeth, both deciduous and permanent, as well as spaces within the teeth.

Furthermore, the CPU 10 may be programmed to recognize certain anatomic and morphological variations characteristic of various teeth such as canines, bicuspids, molars, and incisors as well as variations between deciduous and permanent teeth. These variations also involve various mesio-distal widths as well as clinical crown height differences that characterize deciduous teeth from permanent teeth.

In addition, the system 1 of the present invention may store medical standards within the CPU 10 for various races of human beings. The statistical comparisons may be used for the CPU 10 to determine whether certain teeth are either deciduous or permanent, as well as to determine the sizes of certain teeth in a user's mouth even if the angle at which images are taken are not right angles to the teeth. In fact, the CPU 10 may determine which teeth have been rotated and which have not been rotated. The CPU 10 may evaluate occlusal views as well as foreshortened widths of rotated front teeth. The CPU 10 may then determine which tooth is rotated or not rotated by widths in a frontal view. In addition, the statistical comparisons may aid the CPU 10 in determining the presence of spacing or crowding and the amount of spacing and/or crowding that may be present. In addition, shortage of space due to decay and premature loss of either deciduous teeth with adverse drifting of adjacent adult teeth and/or the loss of permanent teeth or loss of space due to decay or poor eruption, or lack of eruption of teeth with loss of space may also be identified by the CPU 10.

Furthermore, the CPU 10 may determine if the user has any teeth missing. Where a tooth may be missing in the image, and a dark space is identified in place of a tooth, the CPU 10 may determine that a tooth is supposed to be in this area. The CPU 10 may count teeth from the midline and may determine if all teeth are present as well as if a tooth actually belongs in a dark space. If the CPU 10 determines that a tooth belongs in the dark space, the CPU 10 may determine if the space may be adequately sized for a tooth to fit within the space. The CPU 10 may also determine the percentage of foreshortening of the tooth mesial to the space and/or distal to the space. The CPU 10 may determine this percentage by measuring mesio-distally the size of the tooth's image and dividing that size into the size that the tooth should be by the factor estimating its size from the upper central incisor width. The CPU 10 may then calculate the actual mesio-distal distance that exists at the space by multiplying the foreshortened space by this enlargement factor.

In addition, if the images are not taken at right angles, whether the image is a single tooth or a plurality of teeth, the computer program stored within the CPU 10 may allow the CPU 10 to configure the images in such a manner to compensate for the discrepancy.

Moreover, if the user requires a dental appliance, the system 1 of the present invention may size the apparatus to fit the teeth of the user based on the measurement of a single tooth. More specifically, the computer program stored in the CPU 10 may allow the CPU 10 to superimpose an image of a dental appliance over an image of the set of teeth of the user, extrapolated from data related to the image of a single tooth as well as statistics stored within the CPU 10.

In addition to images taken by the ICC 40, the system 1 may query the user as to whether the user experiences sounds or clicks in the temporomandibular joint or joints and may request the user to move his jaw downward and forward to determine if the sound or click is no longer present. The system 1 may query the user visually, through a display on the monitor 30, or the system 1 may query the user verbally, through a speaker system or the like. The user may be able to respond verbally or by entering information into the IRC 20. Furthermore, the system 1 may determine if a dysfunction of the temporomandibular joint exists by observing the opening of the lower jaw as to its maximum opening.

The system 1 may also determine if the user bites improperly in a forward and/or an incompletely closed position. The system 1 may query the user to close his mouth. If the system 1 determines, by use of the ICC 40 and the CPU 10, that the user has improperly closed his mouth, the system 1 may compensate for this by adjusting the image of the upper jaw and the lower jaw by, for example, realigning the portion of the image containing the lower jaw until it is properly aligned with the portion of the image containing the upper jaw of the user. As a result, more accurate estimates of jaw relation, molar relations or overjet may be calculated.

After a diagnosis is reached by the outside source, the CPU 10, or both, the diagnosis may be provided to the user, as shown at step 280. The diagnosis may be given to the user by written means, such as on a sheet of paper dispensed by the system 1. The sheet may include graphical representations of implementation of the appliance in the mouth of the user. Or, the diagnosis may be given to the user by verbal means, such as through a speaker associated with the system 1, or the like. In addition, the diagnosis may be provided to the user as a display on the monitor 30.

In the diagnosis, the system 1 may determine whether the user requires a dental appliance, as shown at step 290. The CPU 10 may be pre-programmed with data denoting the severity of a condition, such as overbite or overjet, for individuals of varying age, race, sex, etc. The CPU 10 may be programmed to classify levels of severity of overbite or overjet as minimal, moderate, or severe based on predetermined dental standards. If the CPU 10 determines that the particular level of severity for the user is treatable by having the user wear a dental appliance, the system 1 may dispense the appropriately sized dental appliance, as shown at step 300. However, if the user does not require a dental appliance and/or the condition of the user cannot be corrected by a dental appliance, the user may be notified by the system 1, as shown at step 280.

After services have been rendered, a user may pay for the services, as shown at step 310. Payment may be made by, for example, a credit card or a debit card. To this end, a user may place the credit card or debit card within the system 1, and the cost of the services may be charged to the card. The system 1 may be connected by, for example, the internet, telephony or other means to another system, such as a financial institution, for example, capable of recording the charges. In another embodiment, payment may be made by receipt of a negotiable instrument or cash by the system 1.

Figure 3:
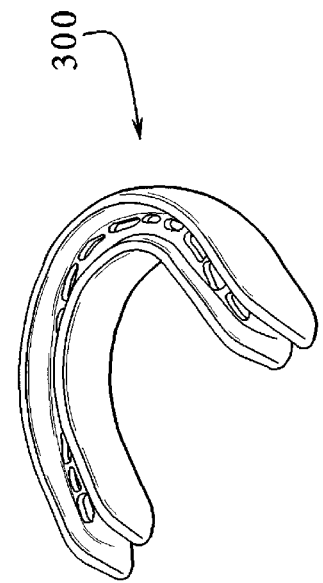
FIG. 3 illustrates a plan view of a dental appliance dispensed by an embodiment of the system of the present invention.

FIG. 3 generally illustrates a dental appliance 300 that may be dispensed by the system 1. The dental appliance 300 may be constructed from, for example, rubber or other material known by those skilled in the art. The dental appliance 300 may correct orthodontic conditions such as overbite, overjet and the like and may be worn in the mouth of a user. The dental appliance 300 may have a plurality of configurations to correct an orthodontic condition, depending on the age and number of adult teeth present in the mouth of the user. Preferably, the system 1 of the present invention stores and/or dispenses three uniquely configured dental appliances for correcting a number of diagnosed conditions. For example, if the orthodontic conditions that may be diagnosed by the system include appliances for correcting an early (4 to 7 year old); a mixed dentition (6 to 12 year old); and an adult case (12 years and older); then the system 1 may store and/or dispense three different dental appliances 300 of several varying sizes of each type, one appliance for each of the age ranges. Of course, the system 1 may be programmed to diagnose any of a plurality of orthodontic conditions with any one of a plurality of dental appliances available within the system 1 to correct the diagnosed condition.

The system 1 may also diagnose what type and size of dental appliance 300 is required for the user based on the number of teeth in the mouth of the user. The system 1 may contain, preferably, three types of dental appliances 300 corresponding, preferably, to users having 20, 24, and 28 teeth in their mouth as measured and extrapolated, for example, from a measurement from a midline to the back of the mouth of the user. Each type of dental appliance 300 may preferably have a plurality of sizes. The system 1 may provide the user with the particular dental appliance 300 for the type and size of dental appliance 300 suitable to correct the orthodontic state of the user.

In another embodiment of the system 1, the system 1 may diagnose the orthodontic state of the user merely from receiving information about the user's age. The user may input his age into the IRC 20. The CPU 10 may then direct the system 1 to dispense a dental appliance 300 of an appropriate type and size for the user based on the age of the user and/or medical standards programmed into the CPU 10.

In another embodiment, the system 1 may use the age of the user to assist in providing a diagnosis. For example, if the CPU 10 receives information that a user has 21 teeth in his mouth, the system 1 may be programmed to determine, for example, that three molars should be present based on the age of the user. The system 1 may then determine that the dental appliance 300 corresponding to a dental appliance for a user with 24 teeth in the mouth of the user is required to correct the orthodontic state of the user.

In another embodiment, the orthodontic state of the user may be diagnosed from an image of a single tooth. In this embodiment, if a front tooth is missing, the system 1 may diagnose the orthodontic state of the user from an image of another tooth in the mouth of the user.

In yet another embodiment, the orthodontic state of the user may be diagnosed from an image of the interior of the mouth of the user in a portion of the mouth of the user from a mid-line to the back of the interior of the mouth of the user. One measurement from a midline back may be made which generally identifies five, six, or seven teeth. From that measurement, the computer evaluates that data to determine whether, for example, 20, 24, or 28 teeth, respectively, are in the mouth of the user.

FIG. 4 illustrates a system 400 having a camera 410 for taking images, whether digital, still, video, digital x-ray, or the like, of the portion of the mouth of the user. The camera 410 may be held, for example, by a set of clamps 420 onto a set of rods 430 held to, for example, a wall by fasteners 440 and may be positioned by the user to a desired height for taking images. The clamps 420 may be designed to frictionally engage the rods 430 and hold the camera 410 in place unless moved by pressure applied to the handles 450 to adjust the height of the camera 410 by, for example, a user. To this end, the user may grasp a set of handles 450 attached to the camera 410 to position the camera 410 to the desired height.

The system 400 may be used, for example, in a pharmacy. The diagnosis may be transmitted to a remote location, by, for example, electronic mail or the like, where an attendant to the system 400, such as, for example, a pharmacist, may provide a dental appliance 300 to the user based upon the diagnosis. Or, the system 1 may notify the user, whether visually by the monitor 30, or other communication means, of the location of the appropriate dental appliance within the pharmacy, drugstore, grocery store, or other like store in which such appliances may be available and/or sold.

FIG. 5 illustrates a side view of a portion of the embodiment illustrated in FIG. 4 wherein the camera 410 is positioned to a desired height. A user 512 may position his head 516 on a chin rest 510 and against a head rest 518. The chin rest 510 and/or the head rest 518 may, for example, be raised or lowered by various means known to those skilled in the art. The camera 410 may be connected to, for example, a CPU 10, which may evaluate images taken by the camera 410 of the portion of the mouth of the user 512. The CPU 10 may be integrally formed with the system 400 or remotely situated from the camera 410 of the system 400.

Figure 6:
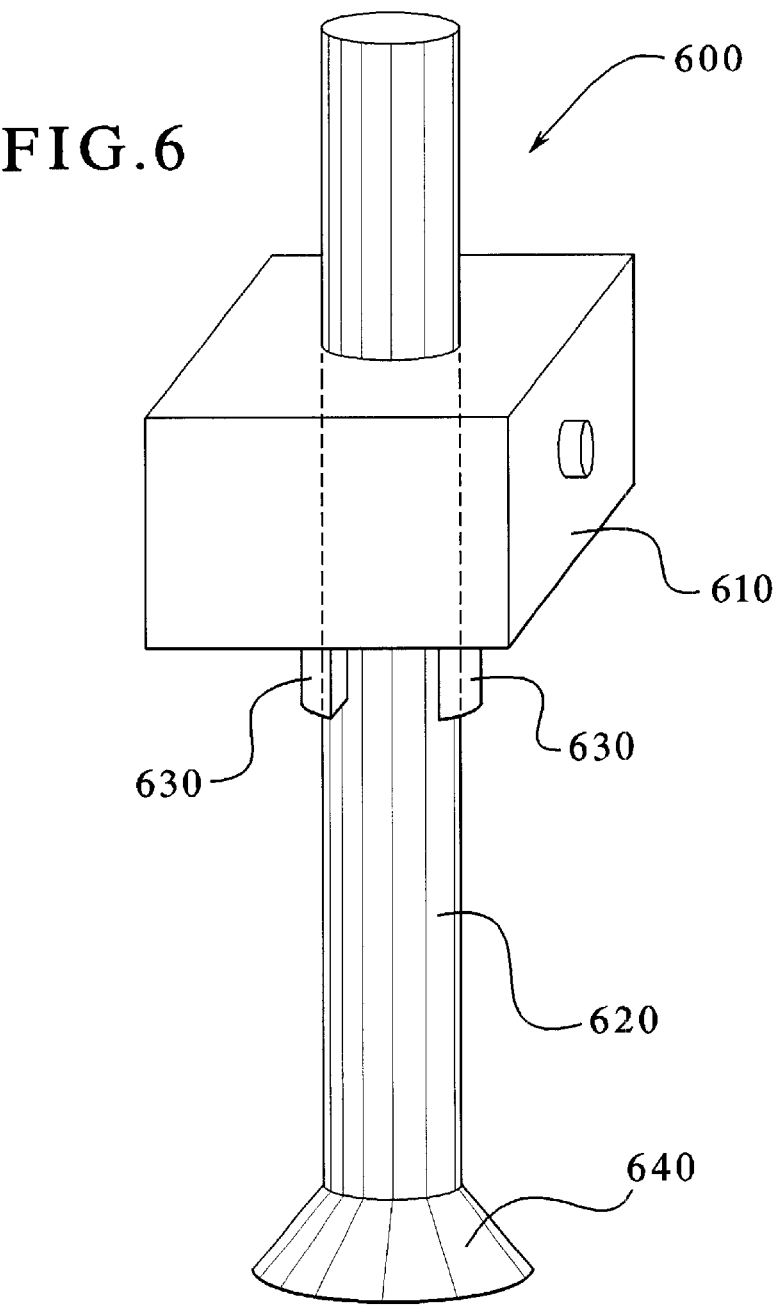
FIG. 6 illustrates a perspective view of an apparatus in an embodiment of the present invention.

FIG. 6 illustrates an embodiment of an apparatus 600 of the present invention in which the camera 610 may be attached, for example, to a rod 620 by, for example, clamps 630. In this embodiment, the apparatus 600 is not attached to a wall and may stand on the base 640 provided, for example, by the rod 620 or other means of support. The user may raise or lower the camera 610 along the rod 620 to a desired height to allow the camera 610 to properly obtain images of the interior of the mouth of the user. The apparatus 600 may also be used, for example, in a pharmacy or other like store.

In another embodiment of the present invention, the system 1 may provide the user with a diagnosis after receiving images via, for example, electronic mail, the internet, or the like. The images may be taken while the user positions a ruler or other measuring device near his face. A second individual may then, using a digital still camera, digital video camera, or the like, capture images of the face and/or profile of the user. Additional images of the user may be taken, including a smiling view from the front of the mouth, right and left sides of the mouth, and/or upper and lower occlusal views. Images may also be taken by the user using any type of remote operation of a digital still or digital video camera or any other method known by those skilled in the art. The images may then be transmitted to a remote location via, for example, electronic mail, the internet, or the like, where a diagnosis may be performed by a CPU or individual to determine whether the user is a candidate for a dental appliance. If the user is a candidate, the type and size of the dental appliance may also be determined by the CPU or individual. The user may then pay for the diagnosis and/or dental appliance by, for example, credit card or the like, by transmitting the credit card number along with the images or disclosing the credit card number by other means known by those skilled in the art.

Figure 7:
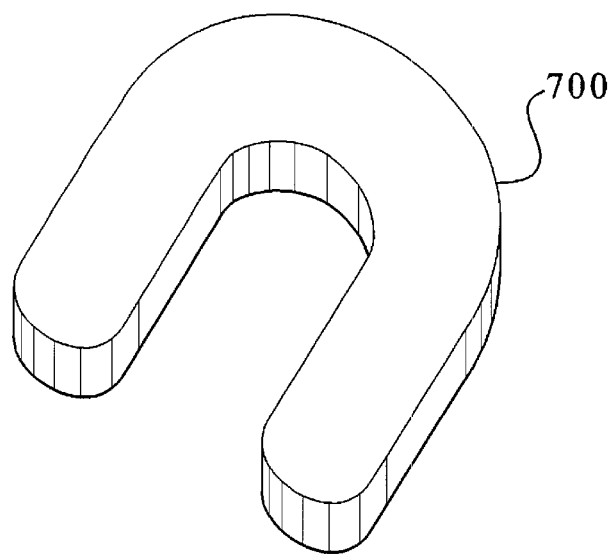
FIG. 7 illustrates a perspective view of an apparatus in an embodiment of the present invention.

FIG. 7 illustrates a wafer 700 that may be implemented in diagnosing the orthodontic condition of the user. The wafer 700 may be constructed from, for example, wax, rubber, plastic, or any other material known by those skilled in the art. The wafer 700 may be obtained by the user from the system 1, or the wafer 700 may be obtained via, for example, responses by the user to advertisements on the internet, television, or radio. In addition, the wafer 700 may be obtained, for example, over-the-counter at, for example, a pharmacy, grocery store, or the like or by direct mailing to the user.

Figure 8:
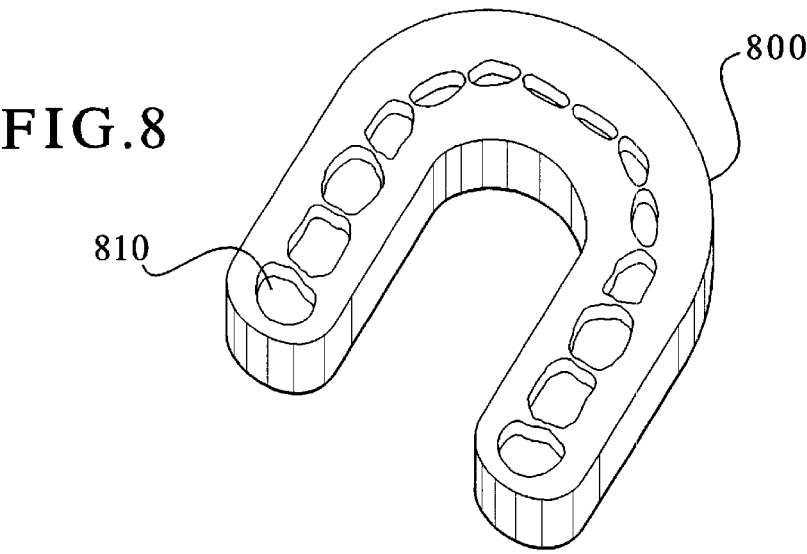
FIG. 8 illustrates a perspective view of an apparatus in an embodiment of the present invention.

FIG. 8 illustrates a wafer 800 that the user may bite into, which may leave an impression 810 in the wafer 800. Once the user has made an impression into the wafer 800, the wafer 800 may be sent to a remote location for a diagnosis. The diagnosis may consist of, for example, pouring plaster, or other material known by those skilled in the art, into the wafer 800 to obtain a positive model of the teeth of the user. A plate which may have a plane, and a bed of pins, with each pin being perpendicular to the plane and capable of positioning along an axis perpendicular to the plane, may be used to conform to the shape of the impression 810 made in the wafer 800 and also provide a positive model of the upper and lower teeth of the user. A proper type and size of dental appliance 300 may then be determined, if necessary, to correct the orthodontic state of the user.

In another embodiment, a depth sensitive photograph may be taken of the wafer 700 after the user bites into the wafer 700. The depth sensitive photograph may provide a three-dimensional image of the upper and lower teeth from which a diagnosis may be obtained.

In another embodiment of the present invention, the images of the mouth of the user may be taken by a photosensitive or pressure-sensitive film which a user may position between the upper jaw and the lower jaw of the user. The film may then provide an image of the upper teeth and the lower teeth. The image may then be transmitted to a remote location by for example, the internet, electronic mail, direct mailing, or the like for diagnosis by a CPU or an individual.

Figure 10:
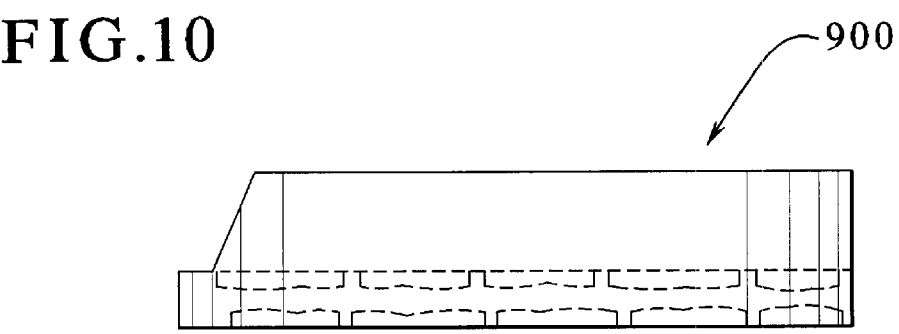
FIG. 10 illustrates a side view of an apparatus in an embodiment of the present invention.
Figure 9:
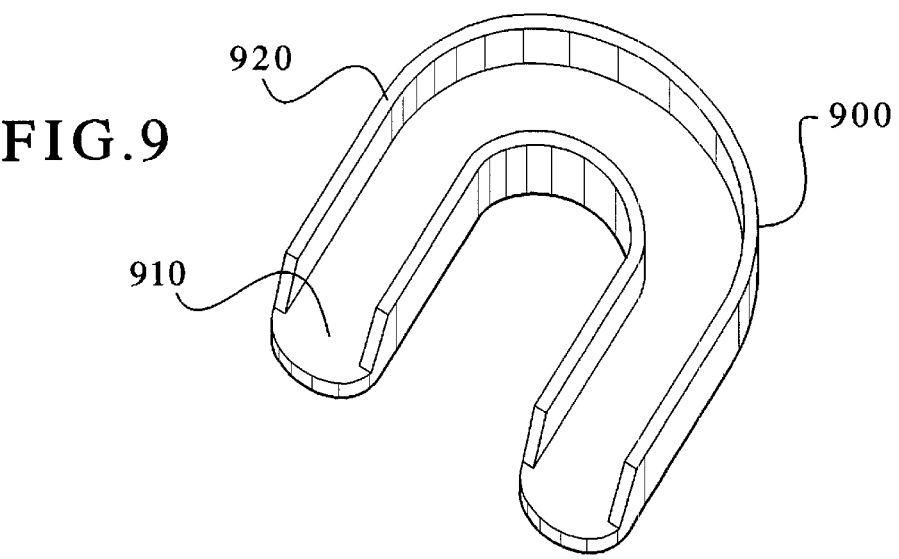
FIG. 9 illustrates a perspective view of an apparatus in an embodiment of the present invention.

FIG. 9 illustrates a tray 900 that may be used to provide a diagnosis to the user in another embodiment of the present invention. The tray 900 may have an interior 910 being flat and an edge 920 which are sized to fit inside the mouth of the user. The interior 910 of the tray 900 may be filled with wax, moldable plastic, or any other material known by those skilled in the art. An impression of the interior of the mouth of the user may be made by the user by biting onto the interior 910 of the tray 900. The tray 900 or an image of the tray 900 may then be sent to a CPU or an individual for a diagnosis. FIG. 10 illustrates a side view of the tray 900.

In addition to the wafer 700 and the tray 900, any type of device known by those skilled in the art and capable of taking an impression of the teeth of the user may be implemented. The impression device could then be sent to an individual for analysis. In addition, an image of the impression device could be taken and may be examined by the CPU 10, a CPU located remote from the system 1, or an individual.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

APPENDIX A

| upp. perm central | = low perm cent | + 3.36 mm (male); | + 3.15 mm (female) |
|---|---|---|---|
| upp. perm lateral | = low perm cent | + 1.22 mm (male); | + 1.22 mm (female) |
| upp. perm lateral | = low perm cent | + 0.53 mm (male); | + 0.53 mm (female) |
| upp. perm canine | = low perm cent | + 2.53 mm (male); | + 2.28 mm (female) |
| upp. perm 1st bic | = low perm cent | + 1.59 mm (male); | + 1.60 mm (female) |
| upp. perm 2nd bic | = low perm cent | + 1.40 mm (male); | + 1.37 mm (female) |
| upp. perm 1st mol | = low perm cent | + 5.39 mm (male); | + 5.27 mm (female) |
| upp. perm 2nd mol | = low perm cent | + 4.93 mm (male); | + 4.06 mm (female) |
| upp. perm canine | = low perm cent | + 1.54 mm (male); | + 1.22 mm (female) |
| upp. perm 1st bic | = low perm cent | + 1.65 mm (male); | + 1.62 mm (female) |
| upp. perm 2nd bic | = low perm cent | + 1.87 mm (male); | + 1.77 mm (female) |
| upp. perm 1st mol | = low perm cent | + 5.76 mm (male); | + 5.49 mm (female) |
| upp. perm 2nd mol | = low perm cent | + 5.34 mm (male); | + 5.09 mm (female) |

TABLE 4

Statistics for Lower Permanent Central Incisor (Deciduous Teeth)

| upp. dec lateral | = low perm cent | + 0.10 mm (male); | − 0.02 mm (female) |
|---|---|---|---|
| upp. dec canine | = low perm cent | + 1.46 mm (male); | + 1.42 mm (female) |
| upp. dec central | = low perm cent | + 1.13 mm (male); | + 1.19 mm (female) |
| upp. dec 1st mol | = low perm cent | + 1.70 mm (male); | + 1.70 mm (female) |
| upp. dec 2nd mol | = low perm cent | + 3.66 mm (male); | + 3.59 mm (female) |
| low. dec lateral | = low perm cent | − 0.68 mm (male); | − 0.62 mm (female) |
| low. dec canine | = low perm cent | + 0.50 mm (male); | + 0.49 mm (female) |
| low. dec 1st mol | = low perm cent | + 2.38 mm (male); | + 2.40 mm (female) |
| low. dec 2nd mol | = low perm cent | + 4.41 mm (male); | + 4.39 mm (female) |

TABLE 5

Statistics for Upper Permanent Central Incisor (Deciduous Teeth)

| upp. dec lateral | = upp dec cent | − 1.01 mm (male); | − 1.21 mm (female) |
|---|---|---|---|
| low. dec canine | = upp dec cent | − 2.47 mm (male); | − 2.46 mm (female) |
| low. dec lateral | = upp dec cent | − 1.81 mm (male); | − 1.81 mm (female) |

I claim:

1. An apparatus for providing a diagnosis of an orthodontic state of a user and dispensing one of a plurality of differently sized dental appliances worn in a mouth of the user wherein a portion of the plurality of differently sized dental appliances are included within each of three orthodontic states, the apparatus comprising:

an image capturing device wherein the image capturing device obtains an image of a portion of the mouth of the user and produces a signal indicative of the image; and a central processing unit programmed with data regarding orthodontic conditions wherein the central processing unit classifies the signal sent by the image capturing device into one of the three orthodontic states wherein one of the plurality of differently sized dental appliances is dispensed for the orthodontic state of the user.

2. The apparatus of claim 1 further comprising:

input means for entering information into the central processing unit.

3. The apparatus of claim 1 further comprising:

a payment device programmed to receive payment from the user.

4. The apparatus of claim 1 wherein the image of the portion of the mouth of the user is an image of a single tooth of the user.

5. The apparatus of claim 1 wherein the central processing unit is located remote from the image capturing device.

6. The apparatus of claim 1 wherein the portion of the mouth of the user is from a midline of a set of teeth of the user to a back portion of an interior of the mouth of the user.

7. An apparatus for providing a diagnosis of an orthodontic state of a user, the apparatus comprising:

an image capturing device wherein the image capturing device obtains an image of a portion of a mouth of the user and produces a signal indicative of the image; and a central processing unit programmed with data regarding orthodontic conditions wherein the central processing unit provides a diagnosis to the user of the orthodontic state of the user based on the image obtained by the image capturing device wherein the portion of the mouth of the user is a single tooth of the user.

8. The apparatus of claim 7 further comprising:

input means entering information into the central processing unit.

9. The apparatus of claim 7 further comprising:

a payment device programmed to receive payment from the user.

10. The apparatus of claim 7 wherein the central processing unit is programmed with data regarding orthodontic conditions wherein the central processing unit classifies the signal sent by the image capturing device into a plurality of orthodontic states.

11. The apparatus of claim 7 wherein the central processing unit is located remote from the image capturing device.

12. An apparatus for providing a diagnosis of an orthodontic state of a user, the apparatus comprising:

an image capturing device wherein the image capturing device obtains an image of a portion of the mouth of the user wherein the portion of the mouth of the user is from a midline of a set of teeth of the user to a back portion of an interior of the mouth of the user, the image capturing device producing a signal indicative of the image; and a central processing unit programmed with data regarding orthodontic conditions wherein the central processing unit classifies the signal sent by the image capturing device into a plurality of orthodontic states.

13. The apparatus of claim 12 further comprising:

input means for entering information into the central processing unit.

14. The apparatus of claim 12 further comprising:

a payment device programmed to receive payment from the user.

15. The apparatus of claim 12 wherein the central processing unit is located remote from the image capturing device.

16. A system for providing a diagnosis of an orthodontic state of a user, the system comprising:

an apparatus having an image capturing device wherein the image capturing device obtains an image of a portion of a mouth of the user wherein the apparatus further has a data transmission device that transmits a signal indicative of the image; and a central processing unit located remote from the apparatus programmed with statistical data regarding orthodontic conditions wherein the central processing unit communicates with the apparatus and receives the signal from the apparatus and further wherein the central processing unit classifies the signal sent by the image capturing device into one of a plurality of orthodontic states.

17. The system of claim 16 further comprising:

input means for entering information into the data transmission device.

18. The system of claim 16 further comprising:

a payment device programmed to receive payment from the user.

19. The system of claim 16 wherein the central processing unit is programmed with data regarding orthodontic conditions wherein the central processing unit classifies the signal sent by the image capturing device into a plurality of orthodontic states.

20. The system of claim 16 wherein the central processing unit is programmed to diagnose the orthodontic state of the user based on the age of the user.

21. The system of claim 16 wherein the portion of the mouth of the user is a single tooth of the user.

22. A method for providing a diagnosis of an orthodontic state of a user, the method comprising the steps of:

providing one of a plurality of differently sized dental appliances wherein one of the dental appliances is worn in the mouth of the user;

providing an image capturing device wherein the image capturing device obtains an image of the portion of the mouth of the user and produces a signal indicative of the image;

providing a central processing unit programmed with data regarding orthodontic conditions wherein the central processing unit classifies the signal sent by the image capturing device into one of three orthodontic states defined by ranges within an orthodontic condition wherein a portion of each of the plurality of differently sized dental appliances are included within each one of the three orthodontic states;

obtaining the image of the portion of the mouth of the user; and transmitting the image to the central processing unit.

23. The method of claim 22 wherein the image of the portion of the mouth is of a single tooth of the user.

24. The method of claim 22 wherein the central processing unit is located remote from the image capturing device.

25. The method of claim 22 wherein the portion of the mouth is from a single tooth of the user to a midline of the user.

26. A method for providing a diagnosis of an orthodontic state of a user, the method comprising the steps of:
providing an image capturing device wherein the image capturing device obtains an image of a portion of the mouth of the user and produces a signal indicative of the image;
providing a central processing unit programmed with data regarding orthodontic conditions wherein the central processing unit provides a diagnosis to the user of the orthodontic state of the user based on the signal transmitted by the image capturing device;
obtaining the image of the portion of the mouth of the user wherein the portion of the mouth is a single tooth of the user; and
transmitting the image to the central processing unit.

27. The method of claim 26 wherein the central processing unit is programmed with data regarding orthodontic conditions wherein the central processing unit classifies the signal sent by the image capturing device into a plurality of orthodontic states.

28. The method of claim 26 wherein the central processing unit is located remote from the image capturing device.

29. A method for providing a diagnosis of an orthodontic state of a user, the method comprising the steps of:
providing an apparatus having an image capturing device wherein the image capturing device obtains an image of a portion of a mouth of the user, the apparatus further having a data transmission device capable of transmitting a signal indicative of the image or a set of data of the user to a central processing unit;
providing a central processing unit located remote from the apparatus programmed with statistical data regarding orthodontic conditions;
obtaining the image of the portion of the mouth of the user; and
transmitting the image to the central processing unit wherein the central processing unit classifies the signal sent by the image capturing device into one of a plurality of orthodontic states.

30. The method of claim 29 wherein the portion of the mouth of the user is a single tooth of the user.

31. The method of claim 29 wherein the portion of the mouth of the user is from a midline of a set of teeth of the user to a back portion of an interior of the mouth of the user.

32. The method of claim 29 wherein the central processing unit is programmed to diagnose the orthodontic state of the user based on the age of the user.

33. The method of claim 29 wherein the central processing unit is programmed with data regarding orthodontic conditions wherein the central processing unit classifies the signal sent by the image capturing device into a plurality of orthodontic states.

34. A method for providing a diagnosis of an orthodontic state of a user, the method comprising the steps of:
providing an image capturing device wherein the image capturing device obtains an image of a portion of the mouth ad of the user wherein the portion of the mouth of the user is from a midline of a set of teeth of the user to a back portion of an interior of the mouth of the user, the image capturing device producing a signal indicative of the image;
providing a central processing unit programmed with data regarding orthodontic conditions wherein the central processing unit provides a diagnosis to the user of the orthodontic state of the user based on the signal transmitted by the image capturing device;
obtaining the image of the portion of the mouth of the user wherein the portion of the mouth is a single tooth of the user; and
transmitting the image to the central processing unit.

35. The method of claim 34 wherein the central processing unit is programmed with data regarding orthodontic conditions wherein the central processing unit classifies the signal sent by the image capturing device into a plurality of orthodontic states.

36. The method of claim 34 wherein the central processing unit is located remote from the image capturing device.

37. An apparatus for providing a diagnosis of an orthodontic state of a user, the apparatus comprising:
a data input device that receives input as to an age of the user; and
a central processing unit programmed with data regarding orthodontic conditions wherein the central processing unit diagnoses the orthodontic state of the user based solely on the age of the user.

38. The apparatus of claim 37 wherein the central processing unit is located remote from the image capturing device.

39. A method for providing a diagnosis of an orthodontic state of a user, the method comprising the steps of:
providing an input device;
inputting an age of the user in the input device;
providing a central processing unit programmed with data regarding orthodontic conditions and receiving information from the input device; and
providing a diagnosis to the user of the orthodontic state of the user based solely the age of the user.

40. The method of claim 39 wherein the central processing unit is located remote from the image capturing device.

41. An apparatus for providing a diagnosis of an orthodontic state of a user, the apparatus comprising:
an image capturing device attached to a rod and movable on the rod wherein the image capturing device obtains an image of the portion of the mouth of the user and produces a signal indicative of the image; and
a central processing unit programmed with data regarding orthodontic conditions wherein the central processing unit receives the signal sent by the image capturing device and classifies the signal into a plurality of orthodontic states.

42. The apparatus of claim 41 wherein the central processing unit is located remote from the image capturing device.

43. The apparatus of claim 41 wherein the image is of a single tooth of the user.

44. The apparatus of claim 41 wherein the image is from a midline of teeth of the user to a back portion of the mouth of the user.

45. A method for providing a diagnosis of an orthodontic state of a user, the method comprising the steps of:
providing a wafer;
providing a central processing unit programmed with data regarding orthodontic conditions;
positioning the wafer within a mouth of the user and making an impression of a tooth of the user;
capturing an image of the wafer; and
transmitting the image of the wafer to the central processing unit.

46. A method for providing a diagnosis of an orthodontic state of a user, the method comprising the steps of:
providing a film;

providing a central processing unit programmed with data regarding orthodontic conditions;

positioning the film within a mouth of the user and making an impression of a tooth of the user;

capturing an image of the film; and transmitting the image of the film to the central processing unit.

47. A method for providing a diagnosis of an orthodontic state of a mouth of a user, the method comprising the steps of:

providing a central processing unit programmed with data regarding orthodontic conditions;

providing an image capturing device wherein the image capturing device obtains an image of a portion of the mouth of the user;

transmitting the image of a portion of the mouth of the user to the central processing unit; and altering the image to compensate for improper closure of the mouth of the user.

48. A method for providing a diagnosis of an orthodontic state of a user, the method comprising the steps of:

providing a tray;

providing a central processing unit programmed with data regarding orthodontic conditions;

positioning the tray within a mouth of the user and making an impression of a tooth of the user;

capturing an image of the tray; and transmitting the image of the tray to the central processing unit.

49. An apparatus for providing a diagnosis of an orthodontic state of a user, the apparatus comprising:

an image capturing device wherein the image capturing device obtains an image of a portion of the mouth of the user and produces a signal indicative of the image;

a focusing mechanism by which the image capturing device is able to focus; and a central processing unit programmed with data regarding orthodontic conditions and further programmed to diagnose the orthodontic state of the user based on a distance between the focusing mechanism and the user.

50. A method for providing a diagnosis of an orthodontic state of a user, the method comprising the steps of:

providing an image capturing device wherein the image capturing device obtains an image of a portion of the mouth of the user and produces a signal indicative of the image;

providing a focusing mechanism by which the image capturing device is able to focus;

providing a central processing unit programmed with data regarding orthodontic conditions and further programmed to diagnose the orthodontic state of the user based on a distance between the focusing mechanism and the user;

positioning the focusing mechanism toward the mouth of the user;

obtaining the image of the portion of the mouth of the user; and transmitting the image to the central processing unit.

51. A method for providing a diagnosis of an orthodontic state of a user, the method comprising the steps of:

providing a wafer;

providing an image capturing device wherein the image capturing device obtains an image and produces a signal indicative of the image;

providing a central processing unit located remote from the image capturing device programmed with data regarding orthodontic conditions;

positioning the wafer within a mouth of the user and making an impression of a tooth of the user;

capturing an image of the wafer; and transmitting the image of the wafer to the central processing unit.

52. A method for providing a diagnosis of an orthodontic state of a user, the method comprising the steps of:

providing a tray;

providing an image capturing device wherein the image capturing device obtains an image and produces a signal indicative of the image;

providing a central processing unit located remote from the image capturing device programmed with data regarding orthodontic conditions;

positioning the tray within a mouth of the user and making an impression of a tooth of the user;

capturing an image of the tray; and transmitting the image of the tray to the central processing unit.

53. A method for providing a diagnosis of an orthodontic state of a user, the method comprising the steps of:

providing an impression device capable of obtaining an impression of a tooth of the user;

providing an image capturing device wherein the image capturing device obtains an image and produces a signal indicative of the image;

providing a central processing unit programmed with data regarding orthodontic conditions;

positioning the impression device within a mouth of the user and making an impression of a tooth of the user;

capturing an image of the impression device; and transmitting the image of the impression device to the central processing unit.

54. A method for providing a diagnosis of an orthodontic state of a user, the method comprising the steps of:

providing an impression device capable of obtaining an impression of a tooth of the user;

providing an image capturing device wherein the image capturing device obtains an image and produces a signal indicative of the image;

providing a central processing unit located remote from the image capturing device programmed with data regarding orthodontic conditions;

positioning the impression device within a mouth of the user and making an impression of a tooth of the user;

capturing an image of the impression device; and transmitting the image of the impression device to the central processing unit.

55. An apparatus for providing a diagnosis of an orthodontic state of a user, the apparatus comprising:

an image capturing device wherein the image capturing device obtains an image of a portion of a mouth of the user and produces a signal indicative of the image; and a central processing unit programmed with data regarding orthodontic conditions wherein the central processing unit provides a diagnosis to the user of the orthodontic state of the user based on the image obtained by the image capturing device wherein the portion of the mouth of the user is a single tooth of the user and wherein the central processing unit classifies the signal sent by the image capturing device into a plurality of orthodontic states.

56. A system for providing a diagnosis of an orthodontic state of a user, the system comprising:

an apparatus having an image capturing device wherein the image capturing device obtains an image of a portion of a mouth of the user wherein the apparatus further has a data transmission device that transmits a signal indicative of the image; and a central processing unit located remote from the apparatus programmed with statistical data regarding orthodontic conditions wherein the central processing unit communicates with the apparatus and receives the signal from the apparatus and wherein the central processing unit classifies the signal sent by the image capturing device into a plurality of orthodontic states.

57. A method for providing a diagnosis of an orthodontic state of a user, the method comprising the steps of:

providing an image capturing device wherein the image capturing device obtains an image of a portion of the mouth of the user and produces a signal indicative of the image;

providing a central processing unit programmed with data regarding orthodontic conditions wherein the central processing unit provides a diagnosis to the user of the orthodontic state of the user based on the signal transmitted by the image capturing device;

obtaining the image of the portion of the mouth of the user wherein the portion of the mouth is a single tooth of the user;

transmitting the image to the central processing unit wherein the central processing unit classifies the signal sent by the image capturing device into a plurality of orthodontic states.

58. A method for providing a diagnosis of an orthodontic state of a user, the method comprising the steps of:

providing an apparatus having an image capturing device wherein the image capturing device obtains an image of a portion of a mouth of the user, the apparatus further having a data transmission device capable of transmitting a signal indicative of the image or a set of data of the user to a central processing unit;

providing a central processing unit located remote from the apparatus programmed with statistical data regarding orthodontic conditions;

obtaining the image of the portion of the mouth of the user; and transmitting the image to the central processing unit wherein the central processing unit classifies the signal sent by the image capturing device into a plurality of orthodontic states.

59. A method for providing a diagnosis of an orthodontic state of a user, the method comprising the steps of:

providing an image capturing device wherein the image capturing device obtains an image of a portion of the mouth of the user wherein the portion of the mouth of the user is from a midline of a set of teeth of the user to a back portion of an interior of the mouth of the user, the image capturing device producing a signal indicative of the image;

providing a central processing unit programmed with data regarding orthodontic conditions wherein the central processing unit provides a diagnosis to the user of the orthodontic state of the user based on the signal transmitted by the image capturing device;

obtaining the image of the portion of the mouth of the user wherein the portion of the mouth is a single tooth of the user; and transmitting the image to the central processing unit wherein the central processing unit classifies the signal sent by the image capturing device into a plurality of orthodontic states.

* * * * *